US00PP08328P

United States Patent [19]

van der Knapp

[11] Patent Number: Plant 8,328

[45] Date of Patent: Jul. 27, 1993

[54] CHRYSANTHEMUM PLANT—FUNGLOW CULTIVAR

[75] Inventor: Jacques C. M. van der Knapp, De Lier, Netherlands

[73] Assignee: Fides Beheer B.V., De Lier, Netherlands

[21] Appl. No.: 720,211

[22] Filed: Jun. 24, 1991

[30] Foreign Application Priority Data

Dec. 18, 1990 [FI] Finland ..... CHR 1915

[51] Int. Cl.[5] ..... A01H 5/00

[52] U.S. Cl. ..... Plt./82.2

[58] Field of Search ..... Plt./74, 74.1, 76, 78, Plt./79, 82.2, 82.3

*Primary Examiner*—Howard J. Locker

*Attorney, Agent, or Firm*—Burns, Doane, Swecker & Mathis

[57] ABSTRACT

A new and distinct cultivar of Chrysanthemum plant named Funglow is provided. The new cultivar is a spontaneous mutation of the Funray cultivar (non-patented in the United States). More specifically, the new cultivar forms attractive relatively small bicolored flowers wherein the petals are dark yellow and the disc florets on the distal ends particularly towards the center bear a dark greyed-purple coloration (as illustrated). The infloresence tends to be pyramidal in configuration. The response period of the flowers is approximately eight weeks. The new cultivar is particularly suited for use in the production of a cut anemone spray under greenhouse conditions.

1 Drawing Sheet

SUMMARY OF THE INVENTION

The present invention comprises a new and distinct cultivar of Chrysanthemum, botanically known as *Chrysanthemum morifolium*, Ramat., and hereinafter is referred to by the cultivar name Funglow.

The new Funglow cultivar is a spontaneous mutation of unknown causation which was discovered and carefully preserved during the course of plant selection work which was conducted by me. The new cultivar was discovered during March, 1990 among plants of the Funray cultivar (non-patented in the United States) being grown under my direct supervision at De Lier, The Netherlands. The Funray cultivar was a spontaneous mutation of the Funshine cultivar (U.S. Ser. No. 719,461, filed concurrently herewith.)

It was observed that a plant consistently formed bicolored flowers with dark yellow petals which included dark greyed-purple coloration on the distal ends of the disc florets (as illustrated) unlike the light yellow petals and light brown disc coloration of the Funray cultivar. Also, the leaves of new Funglow cultivar are dark green while those of the parent Funray cultivar are light green, and the growth of the new Funglow cultivar is strongly vegetative which can be contrasted to the less vegetative growth character of the Funray cultivar. All of the other characteristics of this plant were found to be substantially identical to those of the Funray cultivar. Had I not discovered, carefully studied, and preserved this new cultivar, it would have been lost to mankind. This new cultivar is particularly well suited for growing in the production of a cut anemone spray.

It was found that the new cultivar of the present invention:

(a) exhibits attractive relatively small anemone flowers having an overall diameter of approximately 40 mm. wherein the petals are dark yellow and the disc florets particularly towards the center bear a dark greyed-purple coloration on the distal ends, (b) bears flowers in a somewhat pyramidal configuration, (c) exhibits a flower response period of approximately eight weeks, (d) forms attractive dark green foliage, and (e) has the ability to produce flowers of commercially acceptable quality throughout the year in a cut mum production program.

Asexual reproduction of the new cultivar by cuttings as performed at De Lier, The Netherlands, in a controlled environment has demonstrated that the characteristics of the new cultivar as herein disclosed are firmly fixed and are retained through successive generations of asexual propagation.

Funglow has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar is compared to the Improved Funshine cultivar (U.S. Ser. No. 07/719,464, filed concurrently herewith), it is noted that the Improved Funshine cultivar exhibits white petals and a stronger and more intense red coloration on the distal ends of the disc florets than the parent Funshine cultivar. When the new cultivar of the present invention is compared to the Funbeam cultivar (U.S. Ser. No. 07/719,463, filed concurrently herewith), it is noted that the Funbeam cultivar exhibits light red-purple petals, and even more intense coloration on the distal ends of the disc florets than the Improved Funshine cultivar. When the new cultivar of the present invention is compared to the Funrise cultivar (U.S. Ser. No. 07/719,465, filed concurrently herewith), it is noted that the Funrise cultivar exhibits red-purple petals which tend to be slightly darker than those of the Funbeam cultivar and tends to exhibit a less intense red coloration on the distal ends of the disc florets than the Improved Funshine cultivar. When the new cultivar of the present invention is compared to the Funset cultivar (U.S. Ser. No. 07/719,462, filed concurrently herewith), it is noted that the Funset cultivar exhibits very light-red petals and orange-red coloration on the distal ends of the disc florets.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereafter is The R.H.S. Colour Chart of The Royal Horticultural Society, London, England. The color values were determined at 11:00 a.m. to 12:00 noon under natural daylight conditions at De Lier, The Netherlands, during September, 1990. The plants described were grown under standard greenhouse conditions which approximate those commonly utilized for the production of cut mums.

Classification:

*Botanical.*—*Chrysanthemum morifolium* Ramat., cv. Funglow.

*Commercial.*—Cut anemone spray.

Inflorescence

A. Capitulum:

*Form.*—Pyramidal.

*Type.*—Anemone.

*Diameter across face.*—Approximately 40 mm. on average.

*Diameter of flower center.*—Approximately 25 mm. on average.

B. Corolla of ray and disc florets:

*Color (General tonality from a distance of three meters).*—Yellow with dark center.

*Color ray florets (top surface).*—Yellow, Yellow group 12A.

*Color disc florets.*—Greyed-purple group 185A.

C. Reproductive organs:

*Androecium.*—Not present.

*Gynoecium.*—Present in both ray and disc florets.

Plant

A. General appearance:

*Height.*—Approximately 90 cm. on average.

B. Foliage:

*Color (upper surface).*—Yellow-green group 147A.

*Color (under surface).*—Yellow-green group 147B.

I claim:

1. A new and distinct cultivar of Chrysanthemum plant named Funglow, substantially as herein shown and described, which:

(a) exhibits attractive relatively small anemone flowers having an overall diameter of approximately 40 mm. wherein the petals are dark yellow and the disc florets particularly towards the center bear a dark greyed-purple coloration on the distal ends, (b) bears flowers in a somewhat pyramidal configuration, (c) exhibits a flower response period of approximately eight weeks, (d) forms attractive dark green foliage, and (e) has the ability to produce flowers of commercially acceptable quality throughout the year in a cut mum production program.

* * * * *

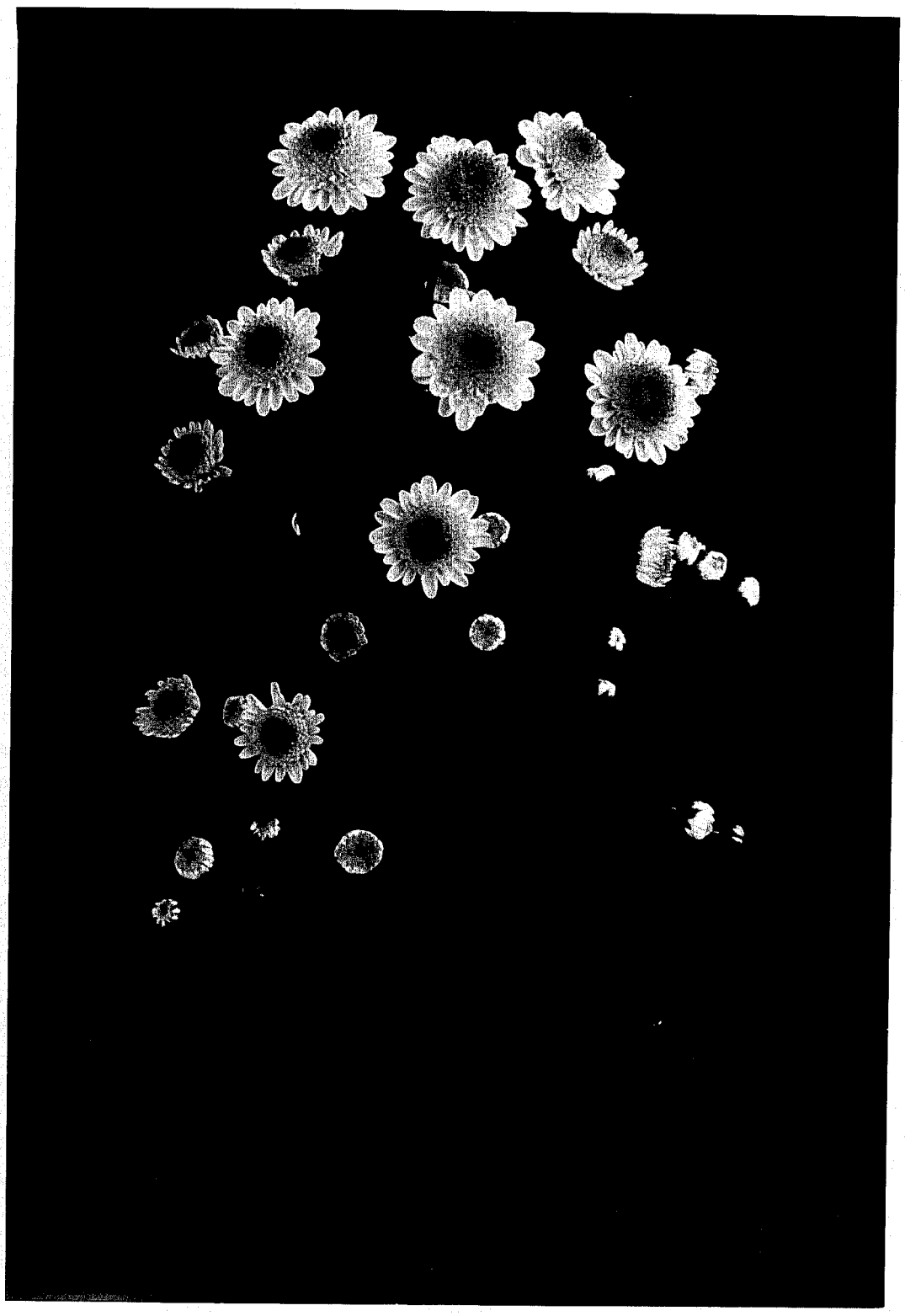

UNITED STATES PATENT AND TRADEMARK OFFICE

CERTIFICATE OF CORRECTION

PATENT NO. : Plant 8,328

DATED : July 27, 1993

INVENTOR(S) : Jacques C.M. van der Knaap

It is certified that error appears in the above-indentified patent and that said Letters Patent is hereby corrected as shown below:

Title page, item

[30] Foreign Application Priority Data reads

December 18, 1990 [FI] Finland ..... CHR 1915. It should read

--December 18, 1990 [HO] Holland ..... CHR 1915 --.

Signed and Sealed this

First Day of February, 1994

Bruce Lehman

*Attest:*

BRUCE LEHMAN

*Attesting Officer*

*Commissioner of Patents and Trademarks*